(12) United States Patent
Johnson et al.

(10) Patent No.: US 8,463,558 B2
(45) Date of Patent: Jun. 11, 2013

(54) ELECTRONIC HAND HELD ION MEASUREMENT DEVICE AND METHOD

(76) Inventors: James R. Johnson, Chandler, AZ (US); Jason R. Johnson, Spokane, WA (US)

(*) Notice: Subject to any disclaimer, the term of this patent is extended or adjusted under 35 U.S.C. 154(b) by 831 days.

(21) Appl. No.: 12/620,355

(22) Filed: Nov. 17, 2009

(65) Prior Publication Data

US 2011/0118988 A1 May 19, 2011

(51) Int. Cl.
*G01N 31/00* (2006.01)
(52) U.S. Cl.
USPC ............................................... 702/25; 702/27
(58) Field of Classification Search
USPC .................... 702/22–25, 27, 30, 31; 436/124, 436/125
See application file for complete search history.

(56) References Cited

U.S. PATENT DOCUMENTS

| 3,648,159 A * | 3/1972 | Stansell et al. ................. 324/438 |
| 2009/0119026 A1* | 5/2009 | Hsiung et al. .................... 702/25 |

* cited by examiner

*Primary Examiner* — Manuel L Barbee
(74) *Attorney, Agent, or Firm* — Parsons & Goltry; Robert A. Parsons; Michael W. Goltry

(57) ABSTRACT

A hand held ion tester includes a housing sufficiently small to be conveniently held in a human hand. A sample chamber is formed in the housing and has a sample inlet in the upper surface of the housing. An ion selective electrode is positioned in the sample chamber so as to be in liquid communication with samples positioned in the sample chamber. A key board and a display are positioned on the upper surface of the housing and a central processing unit contained within the housing is electrically coupled to the ion selective electrode, the key board and the display. The central processing unit is designed and connected to receive signals from the ion selective electrode, process the signals and display processed information on the display.

20 Claims, 4 Drawing Sheets

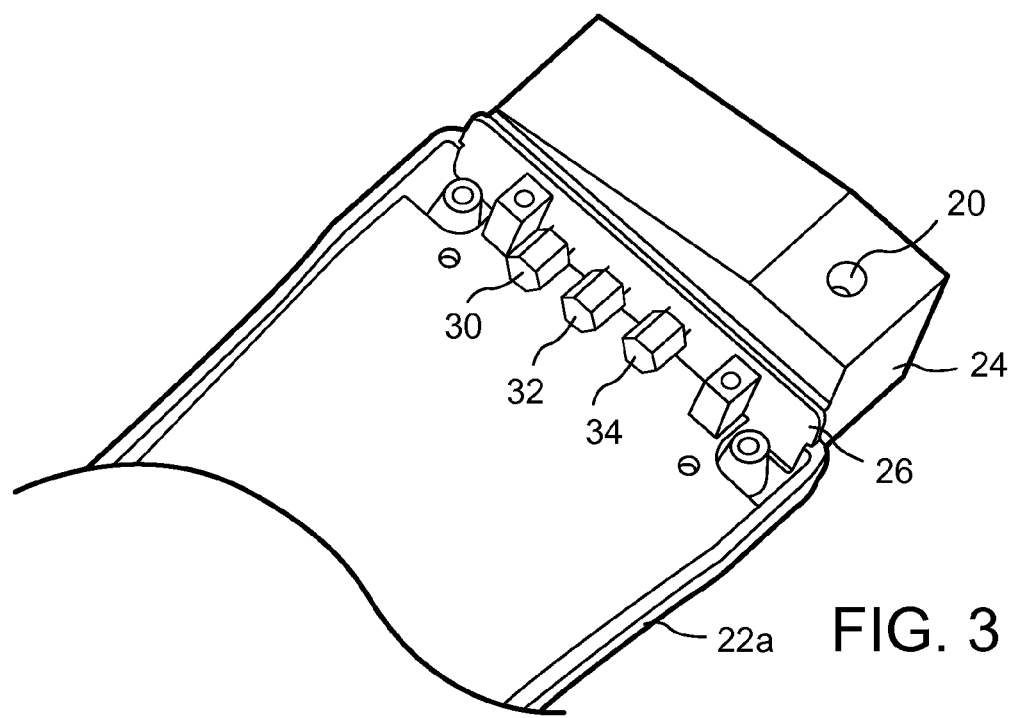
FIG. 3
FIG. 4
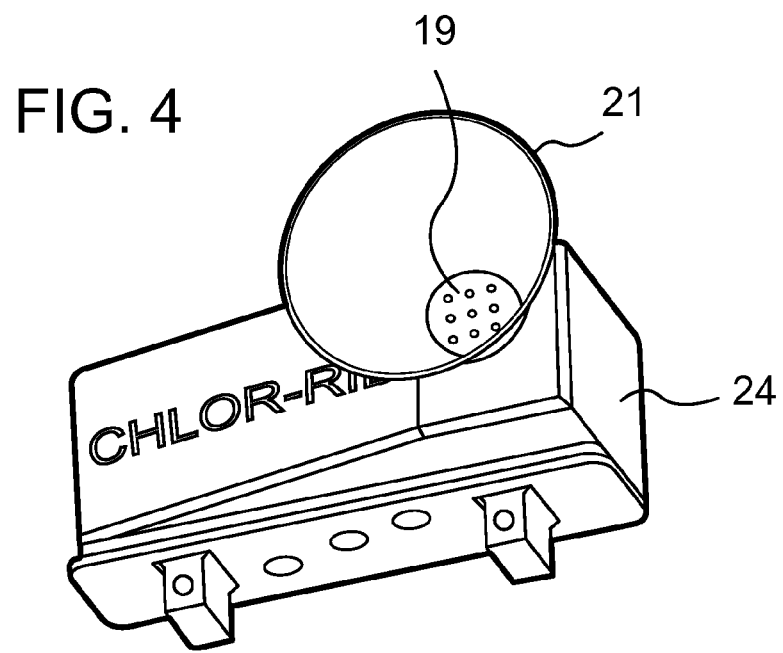

ELECTRONIC HAND HELD ION MEASUREMENT DEVICE AND METHOD

FIELD OF THE INVENTION

This invention relates to hand held ion testers.

More particularly, the present invention relates to hand held ion testers for electronically testing samples for chloride ions.

BACKGROUND OF THE INVENTION

In the prior art, chloride and other ion specific tester systems usually incorporate a meter and an electrode that is on an electrical cord and plugs into the meter. The cord is commonly 3 to 6 feet long and is usually used in a specific testing environment or laboratory. Such a system would be very cumbersome to use in the field and would quickly get damaged. Also, there are integrated instruments for laboratory use but these are large machines that are far too big to be hand held and are not at all suitable for field use.

Further, in all known prior art machines results from various tests or series of tests must be carefully identified and recorded by the operator and stored for later use and study. Each test must be carefully hand recorded along with devising a label describing the specific job and area or surface tested. This record keeping is time consuming and highly subject to errors and miss-labeling.

It would be highly advantageous, therefore, to remedy the foregoing and other deficiencies inherent in the prior art.

An object of the present invention is to provide a new and improved hand held ion tester.

Another object of the present invention is to provide a new and improved hand held ion tester that is easy to use and that automatically records and saves the test information.

Another object of the present invention is to provide a new and improved hand held ion tester that can automatically test a sample of liquid for chloride ions.

Another object of the present invention is to provide a new and improved hand held ion specific tester and method that greatly simplifies data collection and use.

SUMMARY OF THE INVENTION

Briefly, to achieve the desired objects of the present invention in accordance with a preferred embodiment thereof, provided is a hand held ion tester including a housing sufficiently small to be conveniently held in a human hand. A sample chamber is formed in the housing and has a sample inlet conveniently positioned in the upper surface of the housing. An ion specific electrode is positioned in the sample chamber so as to be in liquid communication with samples positioned in the sample chamber. A key board and a display are positioned on the upper surface of the housing and a central processing unit contained within the housing is electrically coupled to the ion selective electrode, the key board and the display. The central processing unit is designed and connected to receive signals from the ion selective electrode, process the signals and display processed information on the display indicative of at least one of the ppm or micrograms/ $cm^2$ of chloride in the sample being tested.

The desired objects of the present invention are further realized in accordance with a more specific embodiment of a hand held ion tester including a housing sufficiently small to be conveniently held in a human hand. A sample chamber is formed in the housing and has a sample inlet conveniently positioned in the upper surface of the housing and a used sample outlet. An ion specific electrode and a pH electrode are positioned in the sample chamber so as to be in liquid communication with samples positioned in the sample chamber. A key board and a display are positioned on the upper surface of the housing and a central processing unit and associated memory are contained within the housing. The central processing unit is electrically coupled to the ion selective electrode, the pH electrode, the key board and the display. The central processing unit is designed and connected to receive signals from the ion selective electrode and the pH electrode, process the signals, display processed information on the display and store the processed information in the memory. A power source, such as batteries or the like, is positioned in the housing and electrically coupled to the central processing unit and the display.

BRIEF DESCRIPTION OF THE DRAWINGS

Specific objects and advantages of the instant invention will become readily apparent to those skilled in the art from the following detailed description of a preferred embodiment thereof taken in conjunction with the drawings, in which:

FIG. 3 is a perspective view of the internal construction of the hand held electronic ion measurement device of FIG. 1;

FIG. 4 is a top perspective view of the measurement component of the hand held electronic ion measurement device of FIG. 1;

DETAILED DESCRIPTION OF THE PREFERRED EMBODIMENT

Figure 1:
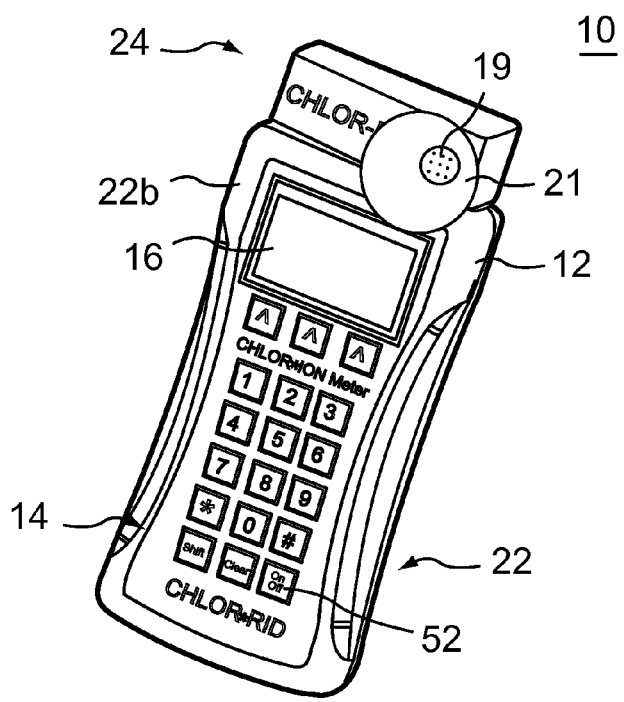
FIG. 1 is a top perspective view of hand held electronic ion measurement device in accordance with the present invention.

Turning now to the drawings in which like reference characters indicate corresponding elements throughout the several views, a hand held electronic ion measurement device 10 is illustrated in accordance with the present invention. While it will be understood that device 10 could be designed with a number of different or additional features and in a variety of physical embodiments and shapes, a simplified version with generally the basic features is illustrated for convenience of understanding.

Device 10 includes a generally rectangular or box-shaped housing 12 with an alpha-numeric key board or control board 14 on/in an upper surface. Also include on the upper surface of housing 12 is a display 16 for showing test results, operating modes, messages, and any other information provided. Display 16 can be any convenient and well known display, such as a liquid crystal display, a light emitting diode display, an organic light emitting diode display, etc. and can be specifically designed in size and shape to display whatever information is desired to be displayed. A sample inlet 20 (see FIG. 3) is formed on the upper surface and is provided with a sample input guide in the shape of a replaceable funnel 21 for convenience in introducing liquid samples to a sample chamber 23, which in this specific embodiment is an elongated tube (see FIG. 6). In this embodiment housing 12 is ergonomically designed to fit conveniently and comfortably into the human hand.

It should be noted that in this embodiment device 10 or housing 12 is actually constructed of two components or segments: a basic control, display and handle or support segment 22 and a measurement segment 24. Further, segment 22 is constructed with a lower part 22a (illustrated in FIG. 3) and a mating upper part 22b. Parts 22a and 22b fit together to form a hollow housing in which the electronics and other parts are mounted. Also, as can be seen best in FIG. 3, measurement segment 24 is constructed to mate with segment 22 at the upper or front end thereof. Internal contacts and/or wiring (not shown) integrate the electronic components of measurement segment 24 with the internal electronic parts of segment 22. While measuring segment 24 is illustrated as a separate element coupled to support segment 22, in this embodiment, it will be understood that measuring segment 24 and support segment 22 can be formed as a single integral piece using common molding techniques.

Referring especially to FIG. 1, it can be seen that funnel 21 includes a screen 19 through which the samples must pass before entering chamber 23 and which removes any debris that may clog the internal operating components. Chamber 23 is in liquid communication with sample inlet 20 and funnel 21 and may be formed as an integral part thereof. An outer end of chamber 23 forms a liquid outlet for device 10 and can include or be attached to a disposal hose through which the samples and flush liquids (explained in detail below) can be captured or dumped.

Figure 5:
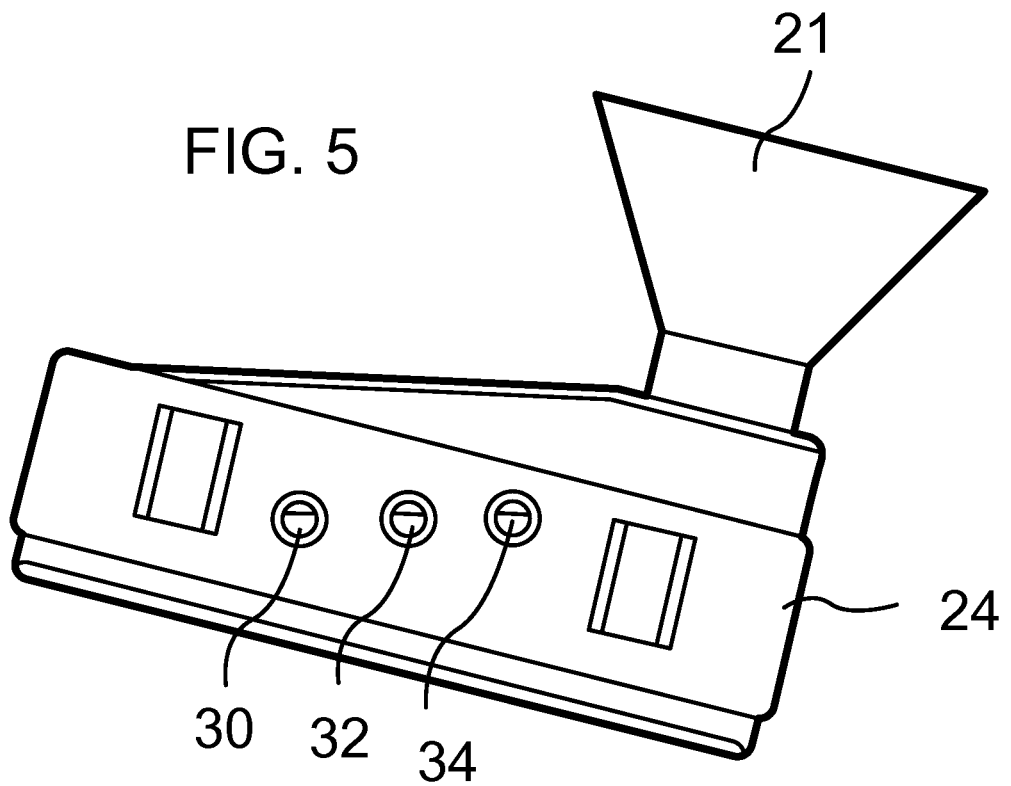
FIG. 5 is a side view of the measurement component of FIG. 4.

Referring specifically to FIG. 3, sample inlet 20 is illustrated with funnel guide 21 removed. Also, a lower wall structure 26 of segment 24 is illustrated. Lower wall structure 26 is constructed to be inserted into grooves in the periphery of the upper end of segment 22 to firmly integrate the two segments together and to complete the enclosure or hollow housing of segment 22. Top and side views of measurement segment 24 are illustrated in FIGS. 4 and 5, respectively. Three electrodes 30, 32, and 34 are mounted in lower wall structure 26 so that measurement or sensitive portions extend into sample chamber 23 and electronic connections thereto extend into the hollow housing formed by segment 22. Also, in FIG. 4 funnel guide 21 is installed and electrodes 30, 32, and 34 are removed to illustrate the feature that the electrodes can be removed for cleaning, repair, or replacement. In this specific embodiment, the three electrodes are a chloride ion selective electrode 30, a pH sensor electrode 32, and a reference electrode 34 for both the pH electrode and the chloride ion electrode. It will be understood that the three electrodes may be interchanged or otherwise shifted in position but are illustrated in a line for convenience (much of the position depending at least in part on the shape of the sample chamber).

Figure 6:
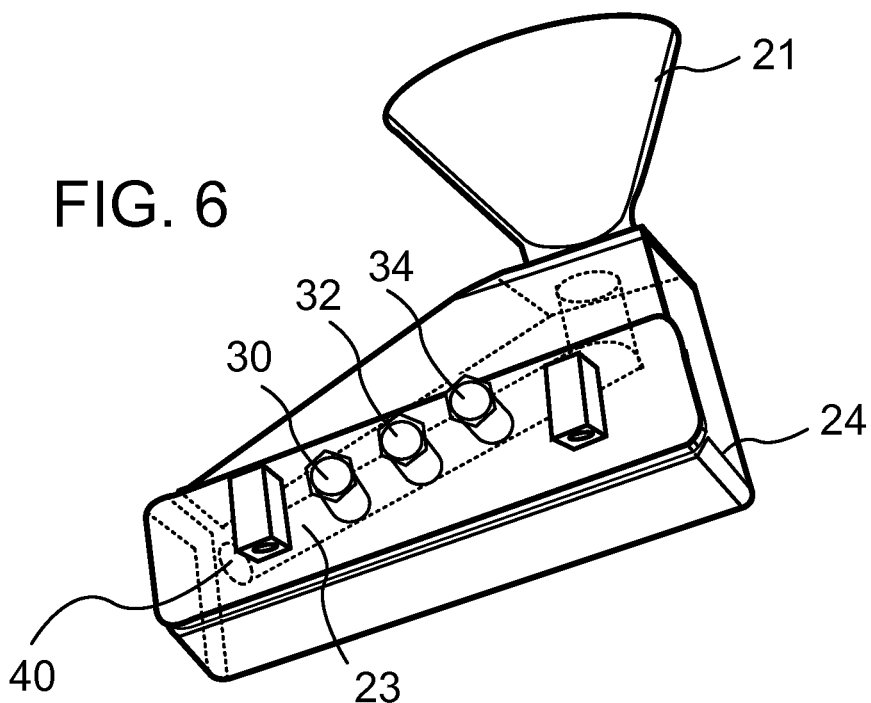
FIG. 6 is a breakaway view illustrating the internal construction of the measurement component of FIG. 4.

Referring specifically to FIG. 6, it can be seen that chamber 23 has an elongated tube-shaped formation with electrodes 30, 32, and 34 spaced along the length thereof. Further, chamber 23 has an external outlet 40 at the lower end thereof. As explained above, external outlet 40 of chamber 23 forms a liquid outlet for device 10 and can include or be attached to a disposal hose through which the samples and flush liquids (explained in detail below) can be captured or dumped. In this specific embodiment ion selective electrode 30 is positioned in chamber 23 near the lower end thereof so that liquid samples passing through chamber 23 come in contact with electrode 30. Also, pH electrode 32 is positioned in chamber 23, preferably (but not necessarily), above electrode 30 so that sample fluids come in contact with pH electrode 31 prior to contacting electrode 30.

In the present embodiment, samples to be tested are simply poured into funnel 21, and flow around and over electrodes 34, 32, and 30 and then exit through external outlet 40. It should be understood that in some applications it may be desirable to provide apparatus for closing chamber 23 during or after tests, cleaning, storage, etc. to this end an electrically or manually operated multi-position control valve (not shown) can be provided at or adjacent external outlet 40 of chamber 23. At least some of the positions can be, for example, test, flush, storage etc. Generally, during storage external outlet can be closed, for example in the present embodiment by means of a mating resilient plug or the like, after which chamber 23 is filled with a storage fluid so that electrodes 30, 32, and 34 do not dry out or become oxidized, etc.

Figure 7:
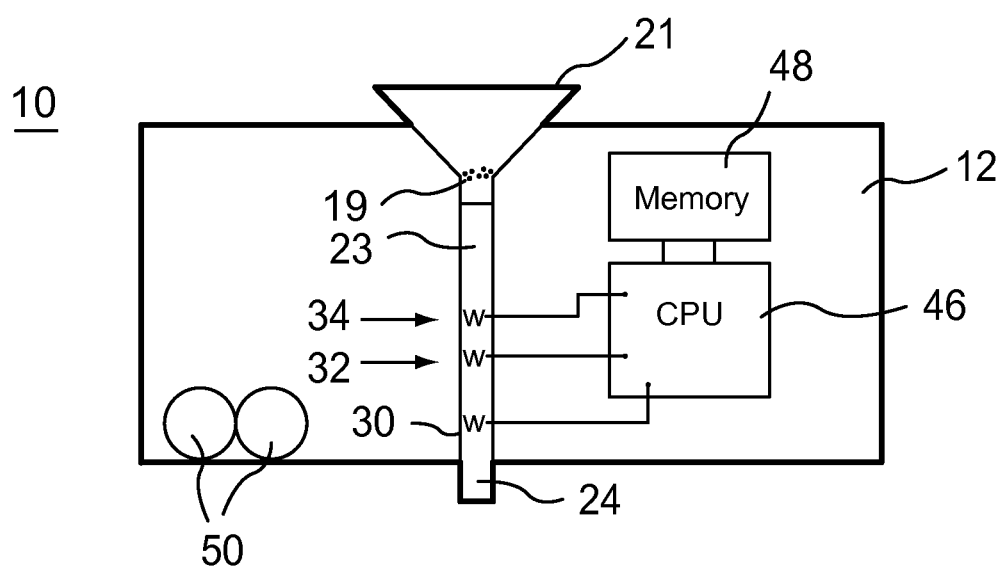
FIG. 7 is a sectional-semi-block diagram of some of the inner components of the hand held electronic ion measurement device of FIG. 1.

Turning now to FIG. 7, which illustrates a simplified block/schematic diagram of the various components, it can be seen that reference electrode 34, pH electrode 32, and chloride ion specific electrode 30 are electronically coupled to a central processing unit (CPU) 46 (such as a microprocessor, specifically designed logic circuitry, etc.). It will be understood that CPU 46 could be any electronic component that can be programmed to perform the various tests and functions described below. CPU 46 is also coupled to a memory 48, which may be external to CPU 46 or contained therein, as known in the art. Also, CPU 46 is coupled to display 16, and keyboard 14. Replaceable batteries 50 are included in housing 12 and are connected through an ON/OFF switch 52 to CPU 46, display 16 and any other components requiring electrical power.

CPU 46 is programmed with software that includes a file system and an operating system that is custom written to device 10 and the electrodes 30, 32, and 34. The software provides the user with a multitude of file and job files that are user created and labeled. The software detects the fluids in chamber 23 and automatically runs tests, in this specific example for the Chloride ion. The pH electrode 32 present a voltage to CPU 46 when a test sample initially contacts it, which voltage is monitored by CPU 46 to determine the specific pH of that test sample. Preferably, any flush liquids used (explained in more detail below) have a known pH level. For each test, readings or signals from chloride ion specific electrode 30 and pH electrode 32 are compared, and calibrated in accordance with the reading from reference electrode 34 to ensure the accuracy of each and every reading. All factory calibrations of electrodes and software have been made with a known liquid, for precision accuracy.

It will be understood by those skilled in the art that test samples can be prepared using a variety of methods including, for example, washing an exact area of the surface to be tested with an exact quantity of water or other solution. With device 10 turned ON (and the multi-position control valve, if present, in the test mode), how ever the test sample is procured or developed, it is introduced into device 10 by pouring it into sample inlet 20 through funnel 21 where it gradually passes over electrodes 30, 32, and 34. Upon contact with the test sample, pH electrode 32 sends a signal to CPU 46 which confirms that a calibrated solution has been introduced. As the test sample reaches electrode 30 a change in voltage reading is detected/read by the software in CPU 46 and data logging is started for a set amount of time as needed to get a ppm and/or micrograms/cm$^2$ reading. As test samples are poured into sample inlet 20 through funnel 21, a voltage reading from electrode 30 will be taken to calculate a ppm and/or micrograms/cm$^2$ with the software program. In the preferred embodiment, the readings are displayed on display 16 after each test and the data is stored in memory 48 for later retrieval.

The software in CPU 46 provides the means for the user to inset job identification and test site location information through keyboard 14, generally prior to making the test, so the test is associated with the information automatically and is completely identifiable. The software may be written to include a variety of location options for each job, that way when the data is downloaded from memory 48 anyone viewing the file can readily identify just what was tested and where. Basically, the data (generally inputted by the user) identifies the project and test location on the project. Test results and locations are stored in memory 48 and are digitally downloadable, typically to a spread sheet. Also device 10 is preferably built capable of blue tooth compatibility.

After each test sample is tested, the multi-position control valve, if present, is moved to the 'flush' mode of operation and the tested sample is discarded. To be sure device 10 is thoroughly clean after performing each test the user pours a flush solution through sample inlet funnel 21, screen 19, and chamber 23, and out end 24. In the 'flush' position, chamber 23 is open to allow the flush liquid to pass directly therethrough and out exterior outlet 40. In some instances, water alone will not clean device 10 adequately, and it requires the use of a flush solution to assure cleanliness so that cross contamination of samples does not occur from test to test. To be sure the proper flush solution is used, pH electrode 32 and the software seek the desired pH and if the desired level is not found display 16 states "incorrect flush agent", or some similar text telling the user to use the proper flush agent. In the preferred operation, water or other flush agents are poured through chamber 23 until a zero reading is obtained from ion specific electrode 30. In this specific embodiment, the software is programmed so that device 10 will not take another test reading until the correct flush agent is passed through the system to clean it or until the zero reading is achieved.

In some instances it may be difficult or impossible to completely clean funnel 21 and screen 19, e.g. after long series of tests, etc. In these instances funnel 21, with screen 19 included, can be simply removed and discarded. A new funnel 21 and screen 19 can then be inserted into sample inlet 20 of chamber 23. Also, as can be seen in FIGS. 3 and 4, if for some reason the electrodes become uncleanable, corroded, etc. they can simply be removed and new electrodes installed.

In this specific embodiment, once testing and flushing has been completed, the exterior outlet of chamber 23 is stopped with a rubber stopper or the like or the multi-position control valve (if present) is moved to the 'storage' position. In the 'storage' mode of operation sample chamber 23 is filled with a fluid to prevent the components and electrodes from drying, corroding, etc.

Figure 2:
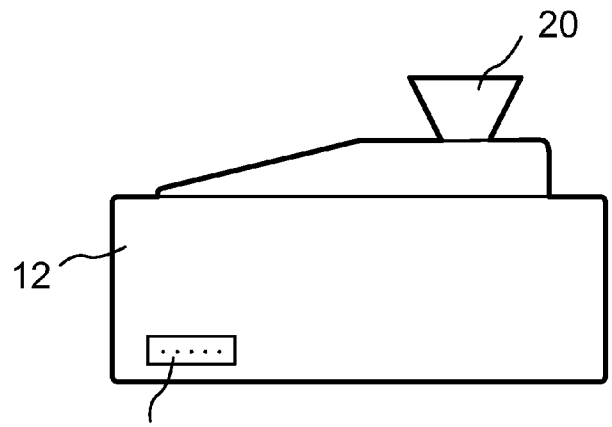
FIG. 2 is an end view of the hand held electronic ion measurement device of FIG. 1.

Also, in the preferred embodiment the software is specifically written to prevent users from deleting tests in a file unless the whole file is deleted. This security measure is included to protect any number of entities and individuals from falsifying test records. At the end of a day or shift the inspector or user can download the data through a USB port 60 (see FIG. 2) to almost any desired software, such as an Excel spreadsheet. The downloaded data can then be electronically shared with job supervisors, asset owners, etc.

Thus, a new and improved hand held ion tester is disclosed that can be easily and conveniently used in the field. The novel combination of hand held tester with ion selective electrode and display or meter is capable of reading the ion content of samples down to as low as 0 ppm. To the best of our knowledge, no meter and testing electrode has ever been integrated into one hand held device for use as a field instrument. The disclosed new and improved hand held ion tester can automatically test and record a sample of liquid for chloride ions. Also, specific methods of testing and recording information are disclosed. The new and improved hand held ion specific tester and method greatly simplifies data collection and use.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A hand held ion tester comprising:
a hollow housing sufficiently small to be conveniently held in a human hand and having an outer surface;
a sample chamber formed in the housing and having a sample inlet extending from the outer surface of the housing and a sample outlet extending to the outer surface of the housing;
an ion specific electrode positioned in the sample chamber so as to be in liquid communication with samples positioned in the sample chamber;
a key board and a display positioned on the housing; and
a central processing unit carried by the housing and electrically coupled to the ion specific electrode, the key board and the display, the central processing unit being designed and connected to receive signals from the ion specific electrode, process the signals and display processed information on the display.

2. A hand held ion tester as claimed in claim 1 further including a power source carried by the housing and electrically coupled to the central processing unit and the display.

3. A hand held ion tester as claimed in claim 1 further including a memory coupled to the central processing unit and designed to receive and store the processed information.

4. A hand held ion tester as claimed in claim 3 wherein the housing further includes a USB port electrically coupled to the central processing unit and positioned to be externally accessible and couplable to external electronics.

5. A hand held ion tester as claimed in claim 1 wherein the display includes one of a liquid crystal display, a light emitting diode display, and an organic light emitting diode display.

6. A hand held ion tester as claimed in claim 1 wherein the sample inlet of the sample chamber includes a screen designed to remove any debris from inputted samples that may clog the internal operating components.

7. A hand held ion tester as claimed in claim 6 wherein the device further includes a removable funnel in liquid communication with the sample inlet and the screen is positioned in the funnel.

8. A hand held ion tester as claimed in claim 1 further including a pH electrode positioned in the sample chamber in liquid communication with samples introduced thereto and electrically coupled to the central processing unit, the pH electrode being designed to provide to the central processing unit a pH signal representative of the pH of samples to be tested in the sample chamber.

9. A hand held ion tester as claimed in claim 1 further including a reference electrode positioned in the sample chamber in liquid communication with samples introduced thereto and electrically coupled to the central processing unit, the reference electrode being designed to provide a reference signal to the central processing unit for each of the samples to be tested in the sample chamber.

10. A hand held ion tester comprising:
a housing sufficiently small to be conveniently held in a human hand and having an outer surface;
a sample chamber formed in the housing and having a sample inlet extending from the outer surface of the housing and a used sample outlet extending to the outer surface of the housing;
an ion specific electrode and a pH electrode positioned in the sample chamber so as to be in liquid communication with samples positioned in the sample chamber;
a key board and a display carried by the housing;
a central processing unit and associated memory carried by the housing, the central processing unit being electrically coupled to the ion selective electrode, the pH electrode, the key board and the display, the central processing unit being designed and connected to receive signals from the ion selective electrode and the pH electrode, process the signals, display processed information on the display and store the processed information in the memory; and
a power source carried by the housing and electrically coupled to the central processing unit and the display.

11. A hand held ion tester as claimed in claim 10 wherein the power source includes a battery.

12. A hand held ion tester as claimed in claim 10 wherein the housing further includes a USB port electrically coupled to the central processing unit and positioned to be externally accessible and couplable to external electronics.

13. A hand held ion tester as claimed in claim 10 wherein the sample inlet of the sample chamber includes a screen designed to remove any debris from inputted samples that may clog the internal operating components.

14. A hand held ion tester as claimed in claim 13 wherein the device further includes a removable funnel in liquid communication with the sample inlet and the screen is positioned in the funnel.

15. A hand held ion tester as claimed in claim 12 further including a reference electrode positioned in the sample chamber in liquid communication with samples introduced thereto and electrically coupled to the central processing unit, the reference electrode being designed to provide a reference signal to the central processing unit for each of the samples to be tested in the sample chamber.

16. A hand held ion tester comprising:
a housing sufficiently small to be conveniently held in a human hand, the housing including an outer surface having an upper surface;
a sample chamber formed in the housing and having a sample inlet in the upper surface of the housing and a used sample outlet extending to the outer surface of the housing;
an ion specific electrode positioned in the sample chamber so as to be in liquid communication with samples positioned in the sample chamber;
a pH electrode positioned in the sample chamber so as to be in liquid communication with samples positioned in the sample chamber;
a reference electrode positioned in the sample chamber so as to be in liquid communication with samples positioned in the sample chamber;
a key board and a display positioned on the upper surface of the housing;
a central processing unit and associated memory contained within the housing, the central processing unit being electrically coupled to the ion specific electrode, the pH electrode, the reference electrode, the key board and the display, the ion specific electrode being designed to provide to the central processing unit a signal representative of the ions present in a sample to be tested in the sample chamber, the pH electrode being designed to provide to the central processing unit a pH signal representative of the pH of the sample to be tested in the sample chamber, and the reference electrode being designed to provide to the central processing unit a reference signal representative of the sample to be tested in the sample chamber;
the central processing unit being programmed to calculate and provide on the display data indicative of at least one of the ppm or micrograms/cm$^2$ of chloride in the sample being tested in response to receiving the signal representative of the ions present in a sample to be tested, the pH signal representative of the pH of the sample to be tested, and the reference signal representative of the sample to be tested; and
a power source positioned in the housing and electrically coupled to the central processing unit and the display.

17. A hand held ion tester as claimed in claim 16 further including a removable funnel positioned in the sample inlet in liquid communication with the sample inlet, and a screen positioned in the funnel and designed to remove any debris from inputted samples that may clog the internal operating components.

18. A hand held ion tester as claimed in claim 16 wherein the housing further includes a USB port electrically coupled to the central processing unit and positioned to be externally accessible and couplable to external electronics.

19. A hand held ion tester as claimed in claim 16 wherein the power source includes a battery.

20. A hand held ion tester as claimed in claim 16 wherein the sample chamber is an elongated tube with the ion specific electrode, the pH electrode, and the reference electrode positioned in spaced apart relationship along the length of the tube.

* * * * *